United States Patent
Williams

(10) Patent No.: US 7,250,529 B2
(45) Date of Patent: Jul. 31, 2007

(54) SYNTHESIS PROCESS FOR 2-(3-HYDROXY-1-ADAMANTYL)-2-OXOACETIC ACID

(75) Inventor: Eric L. Williams, Zachary, LA (US)

(73) Assignee: Albemarle Corporation, Richmond, VA (US)

( * ) Notice: Subject to any disclaimer, the term of this patent is extended or adjusted under 35 U.S.C. 154(b) by 132 days.

(21) Appl. No.: 11/228,055

(22) Filed: Sep. 16, 2005

(65) Prior Publication Data
US 2006/0063950 A1   Mar. 23, 2006

Related U.S. Application Data

(60) Provisional application No. 60/610,893, filed on Sep. 17, 2004.

(51) Int. Cl.
C07C 409/24 (2006.01)
C07C 51/16 (2006.01)
C07C 315/00 (2006.01)
A61K 38/00 (2006.01)

(52) U.S. Cl. .................. 562/6; 562/409; 562/418; 562/427; 514/10

(58) Field of Classification Search .............. 562/6, 562/409, 418, 427; 514/10
See application file for complete search history.

(56) References Cited

FOREIGN PATENT DOCUMENTS

FR           1440245        8/1966
WO    WO 2004/052850 A2    6/2004
WO    WO 2004052850 A2 *   6/2004

OTHER PUBLICATIONS

Enholm, E.J., et al., "1,3-Diastereocontrol in acyclic radical allylations", Tetrahedron Letters 44, 2003, pp. 531-534.
Guette J.P., et al., "No. 665 Preparation et proprietes chiroptiques d'a-glycols R-CHOH-CH$_2$OH$_2$", Bulletin de la Societe Chimique de France, 1972 No. 11, pp. 4217, 4222, 4223, 4224. Not translated.
Hudlicky, M., "Synthesis of Fluorinated a-diketones and Some Intermediates", Journal of Fluorine Chemistry, vol. 18, 1981, pp. 383, 387, 395, 396, 405.
Jaeger, D.A., et al., "Electrophilic Substitution at Saturated Carbon. 52. A model for the proton transfer steps of biological transamination and the effect of a 4-pyridyl group on the base-catalyzed racemization of a carbon acid", Proton Transfer Steps of Biological Transamination, Journal of the American Chemical Society, 101:3, 1979, pp. 717-732.
Manchand, P.S., et al., "Synthesis and antiviral activity of metabolites of rimantadine", J. Med. Chem., 1990, vol. 33, pp. 1992-1995.
Usami K., et al., "Low-temperature photooxygenation of Coelenterate luciferin analog synthesis and proof of 1,2-dioxetanone as luminescence intermediate", Tetrahedron, 1996, vol. 52, No. 37, pp. 12061, 12086, 12090.
Viret, J., et al., "Simple optical resolution of terleucine" Tetrahedron Letters, 1986, vol. 27, No. 48, pp. 5865-5868.

* cited by examiner

Primary Examiner—Thurman K. Page
Assistant Examiner—Lalitha Nagubandi
(74) Attorney, Agent, or Firm—Marcy M. Hoefling

(57) ABSTRACT

A highly advantageous process for the preparation of 2-(3-hydroxy-1-adamantyl)-2-oxoacetic acid or a salt thereof is described. The process comprises subjecting 1-acetyl 3-hydroxyadamantane to liquid phase oxidation with permanganate to produce 2-(3-hydroxy-1-adamantyl)-2-oxoacetic acid or a salt thereof, with acidification to form the free acid when appropriate.

16 Claims, No Drawings

SYNTHESIS PROCESS FOR 2-(3-HYDROXY-1-ADAMANTYL)-2-OXOACETIC ACID

REFERENCE TO RELATED APPLICATION

This application claims the benefit and priority of U.S. Provisional Application No. 60/610,893, filed Sep. 17, 2004, the disclosure of which is incorporated herein by reference.

BACKGROUND

The compound, 2-(3-hydroxy-1-adamantyl)-2-oxoacetic acid, is a desired chemical intermediate for a product under development for potential commercial use by a well-known United States corporation. That corporation wishes to purchase the 2-(3-hydroxy-1-adamantyl)-2-oxoacetic acid for use in its developmental work. There appears to be no published method for synthesizing this compound.

A need thus exists for a simple straightforward synthesis route for preparing 2-(3-hydroxy-1-adamantyl)-2-oxoacetic acid, especially if such a route could result in good yields of the 2-(3-hydroxy-1-adamantyl)-2-oxoacetic acid in a minimum number of synthesis steps.

BRIEF SUMMARY OF THE INVENTION

This invention is deemed to fulfill the foregoing need in an efficient manner. For one thing, the invention utilizes a starting material that can be prepared in high yield by a known prior art synthesis procedure. In addition, the process of this invention is quite simple and straightforward in that it does not require a long series of synthesis steps. Moreover, the process of this invention is readily amenable to scale up to cost-effective industrial scale operation.

Provided by this invention is a process for producing 2-(3-hydroxy-1-adamantyl)-2-oxoacetic acid or a salt thereof, which process comprises subjecting 1-acetyl-3-hydroxyadamantane to liquid phase oxidation with permanganate to produce 2-(3-hydroxy-1-adamantyl)-2-oxoacetic acid, typically in the form of a salt thereof. When the product is formed as a salt, 2-(3-hydroxy-1-adamantyl)-2-oxoacetic acid is readily formed simply by treating the salt of 2-(3-hydroxy-1-adamantyl)-2-oxoacetic acid with a suitable strong acid. The liquid phase can be any non-reactive solvent in which sufficient permanganate can be dissolved to enable the reaction to proceed at a reasonable rate (i.e., to give a yield of at least about 50% and preferably at least about 60% within 24 hours). Preferably, the liquid phase is an aqueous medium (i.e., it contains water with or without one or more non-reactive co-solvents). In whatever solvent medium is selected for use, it is preferred to conduct the oxidation reaction with strong base dissolved or at least partially dissolved in the medium.

One of the preferred embodiments of this invention can be depicted by the following equation:

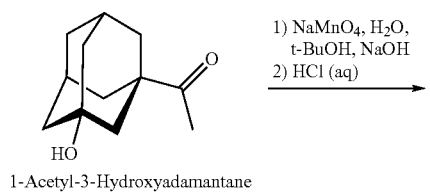

1-Acetyl-3-Hydroxyadamantane

1) $NaMnO_4$, $H_2O$, t-BuOH, NaOH
2) HCl (aq)

-continued

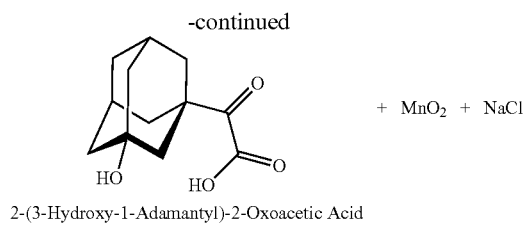

2-(3-Hydroxy-1-Adamantyl)-2-Oxoacetic Acid $+ MnO_2 + NaCl$

These and other embodiments and features of the invention will be still further apparent from the ensuing description and appended claims.

FURTHER DETAILED DESCRIPTION OF THE INVENTION

As noted above, in one of the embodiments of this invention, the permanganate oxidation of 1-acetyl-3-hydroxyadamantane is conducted in at least one non-reactive organic solvent as the medium of the liquid phase. Desirably the solvent and permanganate selected for use in such solvent will provide an acceptable yield in an acceptable reaction period, e.g., a yield of at least about 50% (preferably at least about 60%) of 2-(3-hydroxy acid and/or one or more salts thereof in 24 hours at ambient room temperature.

1-Acetyl-3-hydroxyadamantane

A method for the preparation of the starting material, 1-acetyl-3-hydroxyadamantane, appears in Journal of Medicinal Chemistry, 1990, Vol. 33, pages 1992-1995. The paper reports preparation of this starting material in a 57% yield, and that synthesis starts with the commercially-available 3-hydroxy-1-adamantanecarboxylic acid.

Permanganate Oxidant

Any permanganate salt or mixture of permanganate salts can be used as the permanganate oxidant to effect the oxidation, provided the salt or the mixture thereof is at least partially soluble (but preferably is fully dissolved) in the liquid phase used in conducting the process. Such salts as sodium permanganate, potassium permanganate, lithium permanganate, cesium permanganate, ammonium permanganate, calcium permanganate, strontium permanganate, barium permanganate, cadmium permanganate, silver permanganate, zinc permanganate and various tetraalkylammonium permanganates serve as non-limiting examples of permanganate salts that can be used. The alkali metal and alkaline earth metal permanganates are preferred because of their greater availability and low cost. Sodium permanganate and potassium permanganate are particularly preferred for these reasons, with sodium permanganate being most preferred.

The permanganate functions as a stoichiometric oxidant in the present reaction. Thus the oxidation should be conducted with at least about two moles of permanganate per mole of 1-acetyl-3-hydroxyadamantane used in conducting the reaction. Excess amounts of permanganate can be used, but typically the amount will not exceed about 3 moles per mole of 1-acetyl-3-hydroxyadamantane. Amounts of permanganate somewhat below stoichiometric amounts can also be used. Preferably the permanganate oxidant: 1-acetyl-3-hydroxyadamantane mole ratio used will be in the range of about 1.90:1 to about 2.25:1. More preferably, the permanganate oxidant: 1-acetyl-3-hydroxyadamantane mole ratio used will be in the range of about 1.95:1 to about 2.35:1.

Strong Base

A variety of strong bases can be used to provide basicity to the liquid phase reaction mixture. Inorganic bases that can be used include the alkali and alkaline earth metal oxides, hydroxides, and carbonates. Of these, the hydroxides and oxides of sodium or potassium are preferred, with sodium hydroxide being particularly preferred. Soluble organic bases such as quaternary ammonium hydroxides can also be used in liquid media in which they are soluble or at least partially soluble. Mixtures of two or more inorganic bases, mixtures of two or more organic bases, or mixtures of one or more inorganic bases with one or more organic bases can also be used.

Liquid Phase

In one of the embodiments of this invention the permanganate oxidation of 1-acetyl-3-hydroxyadamantane is conducted in water as the medium. In another embodiment of this invention the permanganate oxidation is conducted in one or a mixture of non-reactive organic solvents as the medium or liquid phase.

In a preferred embodiment of this invention the permanganate oxidation of 1-acetyl-3-hydroxyadamantane is conducted in a mixture of water and at least one non reactive organic co-solvent as the liquid phase. Such mixed solvent systems are advantageous in that use of a mixture of water and a co-solvent as the liquid medium has enabled formation of the 2-(3-hydroxy-1-adamantyl)-2-oxoacetic acid product in higher yields as compared to use of water without a co-solvent. In addition, use of such solvent mixture has resulted in a reduction in solids handling operations.

A liquid phase or medium composed of water alone or with a minor amount (e.g., less than about 50 wt %) of non-reactive organic solvent is desirable when using one or more inorganic permanganate salts and one or more strong inorganic bases in the oxidation reaction as such inorganic salts and bases tend to have good solubility in water. Conversely, a liquid phase medium composed of one or more non-reactive organic solvents alone or with a minor amount (e.g., less than about 50 wt %) of water is desirable when using one or more organic permanganate salts and one or more strong organic bases in the oxidation reaction as such organic salts and bases tend to have good solubility in organic solvents.

One of the features of this invention is that relatively high reactor throughput can be achieved at least when water is used alone or in admixture with one or more non reactive organic solvents in forming the liquid phase reaction medium in which the permanganate oxidation is to be performed. In one embodiment, by using a liquid phase mixture that contains (i.e., is formed from) a relatively high concentration of 1-acetyl-3-hydroxyadamantane, permanganate oxidant, and strong base in the water or mixed solvent composed of water and at least one non-reactive co-solvent, the reactor utilization and reactor throughput will be higher than if the reactor is charged with either a large amount of water alone or with a large amount of a combination of water and one or more non-reactive organic solvents such that the concentration of the 1-acetyl-3-hydroxyadamantane, permanganate oxidant, and strong base in (i.e., charged to) such solvent system in the reactor is relatively low. For example, when the permanganate oxidant used is an inorganic permanganate salt that tends to have relatively poor solubility in organic solvents, the amount of water present in the reaction mixture comprised of or formed from 1-acetyl-3-hydroxyadamantane, permanganate oxidant, strong base, water, and optionally, non-reactive co-solvent(s) can be as low as about 40% by weight based on the total weight of these reactor contents. Since water itself can be used as the sole solvent in the permanganate oxidation reaction mixture, there is no upper limit on the proportion of water relative to organic solvent(s) that can be used when employing such a mixed solvent system. However, to obtain optimum benefits of a solvent system of water and optionally, one or more non-reactive co-solvents, it is recommended that the amount of water present in the reaction mixture comprised of or formed from 1-acetyl-3-hydroxyadamantane, permanganate oxidant, strong base, water, and optionally, co-solvent(s) will typically be no more than about 70% by weight. Thus, where the initial reaction mixture in which the permanganate oxidation is to be conducted is comprised of or formed from water, 1-acetyl-3-hydroxyadamantane, at least one permanganate oxidant, at least one strong base, and optionally at least one non-reactive organic co-solvent, it is desirable that the amount of water fall in the range of about 40-70 wt % based on the total weight of such initial reaction mixture.

When employing inorganic permanganate(s) and inorganic base(s) in the permanganate oxidation reaction, preferably the liquid phase in which such reaction is performed is an aqueous medium, i.e., a liquid medium in which there is at least sufficient water present to dissolve most if not all of the particular inorganic permanganate salt(s) and most if not all of the particular inorganic strong base(s) being employed. If such amount is not already known, it can be determined by a few simple laboratory experiments, as are well known to those skilled in the art. Conversely, when employing organic permanganate(s) and organic base(s) in the permanganate oxidation reaction, preferably the liquid phase in which such reaction is performed is an non-reactive organic medium, i.e., a liquid medium in which there is at least sufficient non-reactive organic solvent present to dissolve most if not all of the particular organic permanganate salt(s) and most if not all of the particular organic strong base(s) being employed. If such amount is not already known, it can be determined by a few simple laboratory experiments, as are well known to those skilled in the art.

When using a mixed solvent system composed of water and at least one non reactive co-solvent, preferably the co-solvent(s) form(s) a single phase liquid medium with water at the temperature and in the proportions being used. More preferably, the co solvent(s) and water are miscible and thus form a single phase liquid at all proportions at least at the temperature(s) being employed in the oxidation reaction. Organic co-solvents which can be used in forming such single-phase mixed solvent aqueous media include for example one or a mixture of ethers, dialkylsulfones, and tertiary alcohols. However it is possible, though less desirable, to have a two-phase liquid medium for the oxidation reaction provided the reaction mixture is suitably agitated during the reaction to enable intimate contact among the components of the reaction mixture. When using such a two-phase system it is preferred to utilize a phase transfer agent such as a crown ether, a cryptand, a poly(ethylene glycol) or a quaternary salt in the liquid phase. A few specific non-limiting examples of phase transfer agents include 18-crown-5,15-crown-5, dibenzo-18-crown-6, dicyclohexano-18-crown-6, Kryptand 211, Kryptand 221, Kryptand 222, cetyl trimethyl ammonium hydroxide, and methyl trioctyl ammonium chloride.

The organic co-solvent is not necessary for the success of the reaction, but in addition to providing improved yields and less solids handling, the co-solvent allows one to introduce the 1-acetyl-3-hydroxyadamantane to the reactor as a liquid which is usually more desirable than performing a solids addition.

Non-limiting examples of suitable co-solvents (or solvents if used in the absence of water) include tert-butanol, tert-pentanol, sulfolane, 1,3-dioxane, 1,4-dioxane, tetrahydrofuran, 2-methyltetrahydrofuran, pyridine, and mixtures of any such co-solvents, as well as analogous non-reactive solvents having suitable water solubility. Tert-butanol is a preferred co-solvent or solvent.

Reaction Conditions

Typically the oxidation reaction is performed at one or more temperatures in the range of about 0° C. to about 60° C., and preferably in the range of about 5° C. to about 40° C., and under ordinary ambient atmospheric pressure conditions. Pressures above or below atmospheric pressure can be used if desired. It is desirable to conduct the reaction with agitation of the reaction mixture. The reaction time is typically in the range of about 1 to about 24 hours, with reactions at higher temperatures being completed in shorter times than reactions performed at lower temperatures.

The manner in which the components of the reaction mixture are introduced into the reaction vessel is not critical. Thus the components can be introduced into the reaction vessel in any order. Usually it is desirable to charge a solution of the 1-acetyl-3-hydroxyadamantane in at least one non-reactive solvent such as the co-solvent discussed above (most preferably tert-butanol) to a mixture of permanganate salt(s) and base(s) fully or at least partially dissolved in water and with or without co-solvent(s) mixed with the water. It is also deemed desirable to have the base(s) in place in the reactor before charging either the 1-acetyl-3-hydroxyadamantane or the permanganate salt(s).

After providing a suitable reaction period including a so-called ride period to allow the reaction to proceed to or towards completion, the resultant reaction mass can be subjected to any suitable workup procedure enabling recovery of the 2-(3-hydroxy-1-adamantyl)-2-oxoacetic acid. Exemplary procedures are set forth in the examples hereinafter.

Acidification

In cases where the oxidation product is formed as a salt and the free acid is desired as the final product, the salt of 2-(3-hydroxy-1-adamantyl)-2-oxoacetic acid or a solution thereof can be treated with a suitable acid, preferably an inorganic acid such as for example, hydrochloric acid, hydrobromic acid, hydroiodic acid, sulfuric acid, or orthophosphoric acid. A suitable strong organic acid such as trifluoroacetic acid may be used, if desired. This acidification (neutralization) to produce the free acid can be conducted before, during, or after other workup steps have been carried out, provided of course that the workup does not result in again forming a salt of 2-(3-hydroxy-1-adamantyl)-2-oxoacetic acid in a case where the free acid has already been formed and is the desired end product. In other words, it is desirable for the acidification, if used, to follow the workup step(s) that involve handling a salt of the desired 2-(3-hydroxy-1-adamantyl)-2-oxoacetic acid. The conditions for the acidification are typical of those commonly used in the chemical arts. Thus ordinary mild temperatures (e.g., up to about 60° C.) and conventional atmospheric pressure conditions are suitable, although any conditions which do not destroy the desired product can be used. Usually a stoichiometric amount of acid sufficient to neutralize all salt (and base if present) or a small excess over the stoichiometric amount will suffice, although greater excesses can be used, if desired.

The following examples illustrate the practice of this invention. These examples are not intended to limit the invention to only what is described therein. The "caustic" referred to therein is of course NaOH.

EXAMPLE 1

Water (20 milliliters (mL)), 10% caustic (17.2 μL), and a 40% sodium permanganate solution (12.0 g) were charged to a 250 mL reactor. The contents were cooled with an ice bath to about 5° C. and a solution of 1-acetyl-3-hydroxyadamantane (5.0 g, 67% assay) in 15 mL of t-butanol was added to the permanganate solution over a 45 minute period. The reaction temperature was controlled between 3° C. and 6° C. during the addition. Following the addition the reaction was stirred with ice cooling at about 5° C. for an additional hour. The mixture was quenched with 10 mL of a 10% sodium sulfite solution, and was filtered through celite. The filtrate was extracted with ethyl acetate (2×50 mL), and the extracts were discarded. The filtrate was acidified with 10 mL of concentrated hydrochloric acid and extracted with ethyl acetate (2×50 mL). The extracts were dried over anhydrous magnesium sulfate and concentrated to give 3.0 grams of a colorless oil that solidified on standing.

EXAMPLE 2

Water (8 mL), 10% caustic (10.3 mL), and a 40% sodium permanganate solution (7.31 g) were charged to a 100 mL reactor. The contents were cooled with an ice bath to about 5° C. and solid 1-acetyl-3-hydroxyadamantane (2.0 g; mp 86-88° C.) was added to the permanganate solution over a 20 minute period. The reaction temperature was controlled between 5° C. and 7° C. during the addition. Following the addition, the reaction was stirred with ice cooling at about 5° C. for an additional three hours. The mixture was quenched with 2 mL of 2-propanol, and was filtered through celite. The filter cake and reaction flask were rinsed with 15 mL of water. The filtrate was extracted with ethyl acetate (30 mL), and the extracts were discarded. The filtrate was acidified with 4 mL of concentrated hydrochloric acid and extracted with ethyl acetate (2×30 mL). The extracts were dried over anhydrous sodium sulfate and concentrated to give 2.0 grams of a white solid. By NMR assay the solid was 82% 2-(3-hydroxy-1-adamantyl)-2-oxoacetic acid resulting in an overall yield of 71%.

EXAMPLE 3

Water (8 mL), 10% caustic (10.3 mL), and a 40% sodium permanganate solution (7.31 g) were charged to a 100 mL reactor. The contents were warmed to 30° C., and a solution of 1-acetyl-3-hydroxyadamantane (2.0 g; mp 86-88° C.) in 8 mL of tert-butanol was added to the permanganate solution over a 30 minute period. The reaction temperature was controlled between 30° C. and 40° C. during the addition. Following the addition, the reaction was stirred at 30-35° C. for an additional three hours. The mixture was quenched with 2 mL of 2-propanol, and was filtered through celite. The filter cake and reaction flask were rinsed with 15 mL of water. The filtrate was extracted with ethyl acetate (30 mL), and the extracts were discarded. The filtrate was acidified with 4 mL of concentrated hydrochloric acid and extracted with ethyl acetate (2×30 mL). The extracts were dried over anhydrous sodium sulfate and concentrated to give 1.95 grams of a white solid. By NMR assay the solid was 94% 2-(3-hydroxy-1-adamantyl)-2-oxoacetic acid resulting in an overall yield of 79%.

Components referred to herein by chemical name or formula, whether referred to the singular or plural, are identified as they exist prior to coming into contact with another substance referred to by chemical name or chemical type (e.g., another component or a solvent). Also, even though the claims hereinafter may refer to substances, components and/or ingredients in the present tense (e.g., "comprises" or "is"), the reference is to the substance, component or ingredient as it existed at the time just before it was first contacted, blended or mixed with one or more other substances, components and/or ingredients in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

This invention is susceptible to considerable variation within the spirit and scope of the appended claims.

That which is claimed is:

1. A process for the preparation of 2-(3-hydroxy-1-adamantyl)-2-oxoacetic acid or a salt thereof, which process comprises subjecting 1-acetyl-3-hydroxyadamantane to oxidation using at least one permanganate oxidant in a liquid phase to produce 2-(3-hydroxy-1-adamantyl)-2-oxoacetic acid or a salt thereof.

2. A process as in claim 1 wherein said liquid phase comprises water.

3. A process as in claim 1 wherein said liquid phase comprises substantially 100 percent water.

4. A process as in claim 1 wherein said liquid phase comprises at least one non-reactive organic solvent.

5. A process as in claim 1 wherein said liquid phase comprises substantially 100 percent at least one non-reactive organic solvent.

6. A process as in claim 1 wherein said liquid phase comprises a mixture of water and at least one non-reactive organic co-solvent.

7. A process as in claim 1 wherein the source of the permanganate oxidant comprises at least one permanganate salt and wherein the mole ratio of said at least one permanganate salt: 1-acetyl-3-hydroxyadamantane used is in the range of about 1.90:1 to about 3:1.

8. A process as in claim 7 wherein the mole ratio of said at least one permanganate salt: 1-acetyl-3-hydroxyadamantane used is in the range of about 1.90:1 to about 2.25:1.

9. A process as in claim 7 wherein the mole ratio of said at least one permanganate salt: 1-acetyl-3-hydroxyadamantane used is in the range of about 1.95:1 to about 2.35:1.

10. A process as in claim 1 wherein the oxidation is conducted in an initial reaction mixture formed from components comprised of water, 1-acetyl-3-hydroxyadamantane, at least one permanganate oxidant, and at least one strong base, and wherein the concentration of said water in said initial reaction mixture is in the range of about 40-70 wt % based on the total weight of said initial reaction mixture.

11. A process as in claim 10 wherein said initial reaction mixture comprises at least one non-reactive organic co-solvent.

12. A process as in claim 11 wherein said at least one non-reactive organic co-solvent comprises tertiary butanol.

13. A process as in any of claims 1, 2, 3, 6, 9, 10, or 11, wherein the source of said permanganate oxidant comprises at least one alkali metal permanganate, wherein said liquid phase comprises dissolved or partially dissolved strong base, and wherein said oxidation is performed at one or more temperatures in the range of about 0° C. to about 60° C.

14. A process as in claim 13 wherein said oxidation is performed at one or more temperatures in the range of about 5° C. to about 40° C.

15. A process as in any of claims 1, 2, 4, 6, or 9, wherein said oxidation produces a product comprised of at least one salt of 2-(3-hydroxy-1-adamantyl)-2-oxoacetic acid or a solution thereof and wherein said at least one salt of 2-(3-hydroxy-1-adamantyl)-2-oxoacetic acid or solution thereof is treated with at least one acid to produce 2-(3-hydroxy-1-adamantyl)-2-oxoacetic acid or a solution thereof.

16. A process as in any of claims 1, 4, 5, or 7 wherein (i) the source of said permanganate oxidant is at least one permanganate salt, (ii) said liquid phase comprises dissolved or partially dissolved strong base, and (iii) said oxidation is performed at one or more temperatures in the range of about 0° C. to about 60° C.

* * * * *